United States Patent
Kannar

(10) Patent No.: US 7,425,342 B2
(45) Date of Patent: Sep. 16, 2008

(54) ODOURLESS GARLIC SUPPLEMENT COMPRISING AN ENTERIC COATING AND A DEODORISING LAYER

(76) Inventor: David Kannar, 182 Belgrave Hallam Road, Belgrave South (AU) VIC 3160

(*) Notice: Subject to any disclaimer, the term of this patent is extended or adjusted under 35 U.S.C. 154(b) by 563 days.

(21) Appl. No.: 10/240,855

(22) PCT Filed: Apr. 6, 2001

(86) PCT No.: PCT/AU01/00390

§ 371 (c)(1),
(2), (4) Date: Jan. 21, 2003

(87) PCT Pub. No.: WO01/76392

PCT Pub. Date: Oct. 18, 2001

(65) Prior Publication Data

US 2004/0170707 A1 Sep. 2, 2004

(30) Foreign Application Priority Data

Apr. 6, 2000 (AU) ................................ PQ6728

(51) Int. Cl.
*A61K 36/8962* (2006.01)
*A61K 36/53* (2006.01)
*A61K 9/00* (2006.01)
*A61K 9/26* (2006.01)
*A61K 9/24* (2006.01)
*A61K 9/48* (2006.01)
*A61K 36/82* (2006.01)
*A61K 36/23* (2006.01)
*A01N 25/34* (2006.01)

(52) U.S. Cl. ............... 424/754; 424/745; 424/400; 424/470; 424/471; 424/408; 424/729; 424/451

(58) Field of Classification Search .......... 424/754, 424/464, 470, 471, 474, 480, 481, 482, 745, 424/747, 729
See application file for complete search history.

(56) References Cited

U.S. PATENT DOCUMENTS

| | | | |
|---|---|---|---|
| 2,512,192 A * | 6/1950 | Yen et al. | |
| 4,377,600 A | 3/1983 | Morinaga | |
| 4,687,667 A * | 8/1987 | Rhodes et al. | |
| 4,849,218 A | 7/1989 | Hess et al. | |
| 4,933,201 A | 6/1990 | Sakai | |
| 5,217,720 A * | 6/1993 | Sekigawa et al. | |
| 5,260,090 A | 11/1993 | Isao | |
| 5,741,524 A * | 4/1998 | Staniforth et al. | |
| 5,804,174 A | 9/1998 | Ishibashi et al. | |
| 5,872,141 A | 2/1999 | Umbreit et al. | |
| 6,270,803 B1 * | 8/2001 | Blatt et al. | |
| 6,620,431 B1 * | 9/2003 | Signorino | |
| 6,787,151 B2 * | 9/2004 | Meijer et al. | |

FOREIGN PATENT DOCUMENTS

| | | | |
|---|---|---|---|
| AU | 691924 | | 12/1995 |
| DE | 3619570 | | 10/1987 |
| DE | 3822962 A | * | 4/1990 |
| JP | 60083573 A | * | 5/1985 |
| JP | 63057532 A | * | 3/1988 |
| JP | 10251143 A | * | 9/1998 |
| JP | 11035439 A | * | 2/1999 |
| JP | 2000004834 A | * | 1/2000 |
| WO | WO 00/20017 | | 4/2000 |

OTHER PUBLICATIONS

Schiewe, F.P. et al., Zeitschrift fur Phythotherapie, 1995, 16(6):343-348. Garlic in hyperlipidemia. Influence of a garlic preparation on the lipid serum levels of patients with primary hyperlipidaemia. Abstract.*
Gleitz, J. et al., Medizinische Welt (1995), 46(8-9): 458-460. Pharmacological relevance of enteric-coated formulation (Allium sativum L. Abstract.*
http://en.wikipedia.org/wiki/Shellac. "Shellac". From Wikipedia, the free encyclopedia. Downloaded Sep. 28, 2005.*
Schiewe, F.P. et al., Zeitschrift fur Phythotherapie, 1995, 16(6): 343-348. Garlic in hyperlipidemia. Influence of a garlic preparation on the lipid serum levels of patients with primary hyperlipidaemia. Abstract.*
Gleitz, J. et al., Medizinische Welt (1995), 46(8-9): 458-460. Pharmacological relevance of enteric-coated formulation (Allium sativum L. Abstract.*
Glietz, J. et al., Medizinische Welt (1995), 46(8-9): 458-460. Pharmocological relevance of enteric-coated formulation (Allium sativum L.). Abstract/.*
Foster et al. (1999) Tyler's Honest Herbal: A Sensible Guide to the Use of Herbs and Related Remedies, Haworth Herbal Press, pp. 171-177.
Koch et al. (1996) Garlic: The Science and Therapeutic Application of *Allium sativum* L. and Related Species, Williams & Wilkins, pp. 92-99 and 114-116.
Schulz et al. (1998) Rational Phytotherapy: A Physicians' Guide to Herbal Medicine, Springer-Verlag, pp. 10-13 and 106-125.
Weiss (1988) Herbal Medicine, Beaconsfield Publishers, pp. 170-175.

* cited by examiner

*Primary Examiner*—Michele Flood
(74) *Attorney, Agent, or Firm*—Hahn Loeser & Parks LLP; John J. Cunniff

(57) ABSTRACT

A garlic supplement comprising: (a) one or more cores comprising garlic; (b) an enteric coating encasing the core(s) which is insoluble at pH less than about 5 but soluble at a pH greater than about 5; and (c) a deodorizer applied external of the core.

18 Claims, 3 Drawing Sheets

ODOURLESS GARLIC SUPPLEMENT COMPRISING AN ENTERIC COATING AND A DEODORISING LAYER

FIELD OF THE INVENTION

This invention relates to an improved garlic supplement with reduced breath odor effects.

BACKGROUND OF THE INVENTION

In this specification, where a document, act or item of knowledge is referred to or discussed, this reference or discussion is not an admission that the document, act or item of knowledge or any combination thereof was at the priority date:
 (i) part of common general knowledge; or
 (ii) known to be relevant to an attempt to solve any problem with which this specification is concerned.

Garlic is utilized in many food cultures for its distinctive flavor. It has also been of interest in medicine for many years and has recently recaptured the interest of the public and of modern Western medical science. This is primarily because of garlic's relatively high sulfur content, historic antibacterial use and reported protective effects on the cardiovascular system.

During the last decade epidemiological, in vivo and in vitro studies, have suggested important cardioprotective properties associated with an increase of garlic in the diet including:
 a) reduction of blood cholesterol levels which may assist in treating hypercholesterolaemia which is a major risk factor for heart disease;
 b) increase of antioxidant activity which assists in reduction of atherosclerosis and lowering of blood viscosity;
 c) decrease in blood pressure and hardening of the aorta;
 d) potential protection against breast cancer;
 e) inhibition of blood clotting and reduction in platelet aggregation;
 f) reduction in blood glucose levels; and
 g) protection against ventricular tachycardia, and fibrillation during ischaemia and reperfusion.

As a result of the recognition of these health benefits, garlic supplements have become popular in the market. These supplements are available as garlic powders, oil macerates, steam distilled oils and aged garlic extracts. Fresh garlic and dried powders are typically used in food preparation and as spices but may also be presented as tablets. Steam distilled oils and aged extracts are used in tablets, soft gelatin capsules or liquids.

Actives and Dosage

When a garlic bulb is crushed, allinase found in vacuoles reacts with S-alk(en)ylcysteine sulfoxide within the cell, forming sulfenic acids which spontaneously convert to thiosulfinates including allicin. The thiosulfinates further degrade to vinyl dithins and ajoenes within 24 hours. The thiosulfinate allicin accounts for approximately 70% of the total thiosulfinates produced and is thought to be the principle bioactive compound responsible for the health promoting benefits of garlic.

Most of the cardio-protective and antibacterial effects of garlic seem to be derived from allicin, its metabolites and to a lesser extent the dialkyl sulfides. The ajoenes have been shown to be powerful inhibitors of platelet aggregation. The most conclusively shown beneficial effect is a reduction of low density lipoprotein and total cholesterol, although the results published to date are variable and inconsistent. Recent evidence suggests that this variation may be due to variability arising from dose formulation causing inconsistent allicin release. These results could be interpreted to mean that the therapeutic efficacy of garlic is dose dependant, relying upon the quantity of allicin released.

As studies have not conclusively shown which phytochemical components are responsible for which beneficial effects provided by garlic, many garlic supplements are currently available on the market such as garlic powders, oil macerates steam distilled oils and aged garlic extracts. Each dose form varies in the phytochemical content because of the different methods of preparation. Even though still relatively inconsistent, the most reproducible cardiovascular benefits seem to be derived from use of fresh garlic and of carefully dried garlic powders.

Therefore, in order to reproduce the historic health benefits of garlic demonstrated in epidemiological studies and maximize therapeutic activity of garlic, the finished product not only needs to be representative of fresh garlic but contain adequate amounts of active phytochemicals, in particular allicin, because efficacy seems dose dependant.

Another factor affecting the efficacy of garlic supplements is the fact that allinase's activity is known to be completely inhibited by the acidic conditions of the stomach. However, the watery alkaline activity in the small intestine does not inhibit allinase activity enabling allicin, other thiosulfinates and/or thiosulfinate metabolites, to be metabolised and transported across the gut mucosa into the portal vein, to reach the liver and cardiovascular system. If allicin and the other thiosulfinates can reach the small intestine they are then able to provide beneficial effects including benefiting the cardiovascular system. Therefore, the garlic supplement should protect allinase from stomach acid.

Garlic Odor

Unfortunately, the consumption of garlic often produces the unsociable 'garlic breath' and general garlic odor. This limits consumption and deprives the public of a therapeutically valuable food, or dietary supplement well recognized for its health promoting benefits. Like many other plant remedies, garlic is a complex mix of biological and phytochemical components, of which the bioactive sulfur compounds have drawn the most attention.

Although allicin is thought to be the principle active compound responsible for providing most of the pharmacological activity of garlic, its metabolic processing by the body to mercaptans is responsible for the characteristic "garlic odor". Allicin is also thought to be responsible for the odor of garlic released in the buccal cavity and upper gastrointestinal tract after consumption. As a result, increasing the dosage of allicin in garlic supplements may cause an increase in garlic odor on the breath.

Some manufacturers have developed formulations to minimize this odor. Odor reducing strategies for garlic supplements have previously included addition of charcoal, titanium dioxide, milk sugar, potato starch, gallic acid or other substances with little success. Odor minimized garlic extracts may also be produced by aging or denaturation of allinase activity. However, minimization of odor may also eliminate many of garlic's active pharmacological compounds and therefore eliminate some of the beneficial effects, for example, aging or denaturation of allinase activity inhibits allicin producing potential. In fact, these deodorized garlic supplements have demonstrated very low efficacy levels.

Parsley has been used in an attempt to reduce the odor of garlic preparations and tablets by mixing the parsley with the garlic in the tablet matrix. The action of parsley is thought to be accomplished by the addition of chlorophyll. The "odor blocking" potency of parsley and chlorophyll has not been previously studied but addition of other strong-smelling volatile oils from thyme, peppermint or other *Lamiaceae* species is thought to mask the strong garlic odor. Green tea extract, standardized to contain polyphenols (catechins), has been tested for deodorizing properties, and found more effective than synthetic deodorants against mercaptan (cause of garlic odor), ammonia, trimethylamine and cigarette smells. Whilst these deodorizing agents do mask the garlic odor to some extent, there is still some odor remaining at a level which many people find objectionable.

Some manufacturers have used an enteric coating to mask the odor of garlic supplements. This has the double advantage of protecting the allinase from the stomach acids until the supplement reaches the small intestine. Whilst enteric coatings have been the most successful method at reducing garlic odor, it has been found that when garlic tablets are consumed daily, an objectionable garlic odor is noticeable in some people after the second day.

While the potential benefits of garlic have been recognized, and many attempts made to provide garlic supplements in a variety of forms including tablets, the odor of garlic has limited the success of these supplements. The previous attempts to in some way alleviate the odors caused by consumption of garlic have not been very successful. There is thus a need for an improved garlic supplement or food to provide beneficial effects for humans and to further reduce the smell of the garlic associated with a high allicin producing garlic powder while maintaining efficacy.

SUMMARY OF THE INVENTION

It has been found that if a garlic supplement has both an enteric coating and a deodorizer then the objectionable garlic odor was considerably reduced. Further, the garlic odor did not return when the garlic supplements were consumed daily for more than two days. The word 'supplement' as used in this description refers to all forms of supplying pharmaceuticals or nutrients orally or enterally. For example, tablets, capsules, oral suspensions, children's formulations, enteral feeds and functional foods.

Accordingly, there is provided a garlic supplement comprising:
(a) one or more cores comprising garlic;
(b) an enteric coating encasing the core(s) which is insoluble at pH less than about 5 but soluble at a pH greater than about 5; and
(c) a deodorizer applied external of the core(s).

Preferably, the garlic supplement or food will be in the form of a tablet, cross linked capsule or gelatin capsule. The garlic may be formed into micro-particles and the enteric-coated micro-particles can then be used in a range of pharmaceutical and food dose forms including hard gelatin capsules, oral suspensions, children's formulations, enteral feeds and functional foods.

The core(s) may in any form including fluid, liquid, solid, gel or mixtures thereof. The core(s) may further comprise carriers suitable for garlic supplements. Such carriers will be known to those skilled in the art. The carrier may be composed of a variety of different binders, fillers, deodorizers, other pharmaceutically acceptable excipients or mixtures thereof.

In order to maximize therapeutic activity of the garlic supplement, the garlic used in the supplement not only needs to be representative of fresh garlic but also needs to contain adequate amounts of pro-active phytochemicals in particular allicin and allinase to optimize allicin and other thiosulfinates producing potential. The garlic may be in any form selected from fresh garlic, dry powder, oils, macerates, extracts, aged extracts, steam distilled oils or mixtures thereof. Such therapeutic activity is maximized by using specialized dehydration techniques and/or specific strains of garlic. Persons skilled in the art will be aware of such dehydration techniques and strains of garlic. One form of garlic which can be used in the supplement is garlic powder although other forms may be possible. Typically, the garlic powder is produced by dehydrating garlic cloves or garlic parts and then crushing the dried garlic to form a powder.

The enteric coating may be selected from the group consisting of cellulose, methylcellulose, natural polymers, synthetic polymers, cross-linked gelatin and mixtures thereof. Preferably, the enteric coating will be cellulose or methylcellulose or a similar substance designed to delay release of the active ingredients. Coating agents are used to protect the tablet core and garlic from the inhibiting effect of the stomach acids. Polymers with pH dependant solubility properties (enteric coatings) have been found to be most useful for this application Cross-linking of gelatin in the hard or soft gelatin capsule is understood to impart the same biological effect. It is also possible to place the garlic core in a capsule which has been enterically coated or cross linked. Each of these methods will delay the release of the garlic powder until the small intestine.

The enteric coating typically has a maximum thickness of up to 0.5 mm or, if the garlic tablet or capsule is for administration to humans, the coating will normally need to comply with USP 2000 standards for delayed release dose forms.

The deodorizer may be either incorporated within the enteric coating or applied as an external coating over the enteric coating. Where the deodorizer is incorporated as an external coating over the enteric coating, this external coating has a thickness in the range of 0.001 mm to 1.500 mm. Typically, when the deodorizer is incorporated into the enteric coating, the weight ratio of deodorizer to the remainder of the enteric coating is in the range of from 0.5 to 1.0%. Preferably, the weight ratio of deodoriser to the remainder of the enteric coating is about 0.6%.

The deodoriser is selected from the group consisting of extracts, aqueous extracts, natural flavours or oils derived from parsley seed, *Lamiaceae* plants, green tea, and flavanoid containing plants or synthetic versions thereof and mixtures thereof. Those skilled in the art will also understand that it is possible to use a variety of other products or combinations of products as a deodorizer. Typically the deodorizer will be incorporated into an additional surface coating such as carnauba wax, polyvinylpyrroldidone, or a sugar, which surface coating may then be applied to the tablet or capsule to form a coating or external layer on the tablet or capsule. Typically the thickness of this outer coating will be from about 0.001 mm to about 1.500 mm. The weight ratio of the deodorizer to the coating as a whole can vary significantly depending on the amount of deodorizer desired for inclusion in the supplement.

It is possible to vary where the deodorizer is located in the supplement. For example, as an alternative, the deodorizer may be incorporated only in the enteric coating; or as a further alternative, the deodorizer may be incorporated in the enteric coating and also in the surface coating. Typically, the deodorizer may be present in amount in the range of 0.5 to 1.0% by weight of the total garlic supplement. Preferably, the amount of deodorizer is about 0.6% by weight of the total garlic supplement.

According to a second aspect of the invention, there is provided a method for preparing a garlic supplement comprising the steps:
(a) forming one or more cores comprising garlic;
(b) encasing the core(s) with an enteric coating which is insoluble at pH less than about 5 but soluble at a pH greater than about 5; and
(c) applying an external coating over the enteric coating wherein the external coating comprises a deodorizer.

According to a third aspect of the invention, there is provided a method for preparing a garlic supplement comprising the steps:
(a) forming one or more core comprising garlic; and
(b) encasing the core(s) with an enteric coating which is insoluble at pH less than about 5 but soluble at a pH greater than about 5 and wherein the enteric coating comprises a deodorizer.

According to a fourth aspect of the invention, there is provided a method for reducing blood cholesterol in patients having high blood cholesterol comprising the step of administering a garlic supplement comprising:
(a) one or more cores comprising garlic;
(b) an enteric coating encasing the core(s) which is insoluble at pH less than about 5 but soluble at a pH greater than about 5; and
(c) a deodorizer applied external of the core(s).

According to a fifth aspect of the invention, there is provided a method for providing reproducible clinical benefits associated with garlic for therapeutic or prophylactic treatment to patients having conditions which benefit from administration of garlic comprising:
(a) one or more cores comprising garlic;
(b) an enteric coating encasing the core(s) which is insoluble at pH less than about 5 but soluble at a pH greater than about 5; and
(c) a deodorizer applied external of the core(s).

DETAILED DESCRIPTION OF THE INVENTION

The garlic powder is in tablet form. It will be readily understood by those skilled in the art that garlic powder can be put in tablet form in a number of different ways. It will be understood that a variety of different binders, fillers and a number of other excipients can be used. An enteric coating is then applied to the tablet by usual methods.

When the tablet formed as detailed above, is swallowed, the tablet moves down the digestive tract to the stomach. As the tablet moves along the upper alimentary tract the outer surface coating (if present) or the enteric coating begins to dissolve and releases deodorizer into the upper alimentary tract. The tablet enters the stomach and further deodorizer is released. The tablet or capsule then passes into the alkaline small intestine, and at this point the enteric coating completely dissolves and allicin produced by the garlic is released. Accordingly, irrespective of whether the deodorizer is contained in a surface coating on the outside of the enteric coating or within the enteric coating itself, or both, a portion of the deodorizer will be released in the upper gut. This is preferred as parts of the deodorizer may react with the garlic released in the lower gut, in particular the allicin, and reduce the potential of the beneficial effects of garlic being provided to the recipient of the tablet or capsule.

Whilst not wishing to be limited by theories, it is postulated that the deodorizer 'dissolved', absorbed, held or metabolized in the upper gut may act locally in the mouth, throat and stomach to reduce garlic odor produced by exhaled garlic derived volatile metabolites. The deodorizer may act to alleviate the odor through either or both of the following two mechanisms:
(a) by deodorizing, that is, the process of adsorbing or reacting with an aromatic substance to render it involatile or non-aromatic, for example, by reacting with any odorous sulfur or garlic derived compound rising from the lower gut or lungs into the buccal cavity; or
(b) by masking, that is, superimposition of a dominant aroma on an undesirable odor so that the undesirable odor was not recognizable.

Accordingly, the enteric coating ensures that all the garlic (and hence allicin) is not released until the small intestine, where it will be most effective. If there is deodorizer in the remaining enteric coating it will also be dissolved at this stage. Any such deodorizer and the garlic will then be digested in the lower gut. At this time the allinase in the garlic powder enzymatically forms sulfenic acids from the S-alk (en)ylcysteine sulfoxides. The sulfenic acids spontaneously convert to thiosulfinates including allicin. Allicin and it's metabolites and other phytochemicals in the garlic are absorbed through the lining of the intestine into the portal vein and/or lymph eventually reaching the arteries, tissue and organs. Non digestible garlic carbohydrates may also remain in the small intestine and act to stimulate beneficial intestinal bacteria including bifidobacteria and lactabacillus and also act broadly as a pre-biotic compound. Once in circulation the allicin, its metabolites and other phytochemicals can provide therapeutic benefits to the human recipient.

The garlic supplement thus provides adequate allicin to the person to produce the beneficial therapeutic effects whilst minimizing the odor of the garlic.

EXAMPLES

The invention will now be further illustrated and explained by reference to the following non-limiting examples.

Preparation of a garlic supplement

Enteric coated garlic tablets with mint are made using the following method.

| Ingredient | Amount |
|---|---|
| Cellulose gum modified NF | 7.50 kg |
| Peppermint extract on micro-crystalline cellulose | 36.00 kg |
| Garlic powder capable of producing 10,000 ppm allicin | 924.00 kg |
| Microcrystalline cellulose, Silicified | 400.50 kg |
| Natural peppermint flavor | 36.00 kg |
| Silicon dioxide, MS | 4.50 kg |
| Stearic acid, acid powder | 45.00 kg |
| Carboxymethyl Starch | 46.50 kg |
| Shellac 20% with Methylcellulose | 215.30 kg |
| Aqueous Peppermint Extract | 14.5 L |

Manufacturing Directions 1.5 kg of peppermint extract is mixed with 4.50 kg of silicon dioxide in a sealed container until uniformly blended (Part A). The remaining peppermint extract (34.50 kg) is then passed through a Sweco separator with 20 mesh screen in a 55 gallon stainless steel drum (Part B). Part A and B are then mixed together in the drum for 10 minutes=Part C.

36.00 kg of natural peppermint flavor and 45.00 kg of stearic acid powder are then passed through a Sweco separator equipped with a 30 mesh screen directly into a 55 gallon stainless steel drum then mixed for 10 minutes=Part D.

924.00 kg of garlic powder is passed through a Sweco separator equipped with a 20 mesh screen and then blended for 10 minutes=Part E.

46.50 kg of carboxymethyl starch, 7.50 kg cellulose gum, and 400.50 kg silicified microcrystalline cellulose are passed through a Sweco separator equipped with a 20 mesh screen then blended for 15 minutes=Part F.

Mix parts C to F and blend.

Tableting Instructions

The blended mixture is loaded into a Gemini tablet press and 2 to 6 tons of pressure is applied. Target weight of each tablet is 625 mg. Target tablet hardness is 25 scu. Target tablet gauge is 0.265 inches.

Coating Instructions

Set inlet air temperature dial to 93° C. Set mistchecker atomization air at 160 SLPM on each gun. Set mistchecker pattern air (total volume) to 240 SLPM on each gun. Turn on exhaust fan. Load each pan with approximately 600,000 tablets and set guns 10 to 12 inches from tablet bed. Jog coating pan until exhaust temperature is 115° F. to 120° F. and adjust pan speed to 6 r.p.m. Pre-mix shellac 20% with methylcellulose and aqueous mint extract to give a conveniently sprayable product then apply 45 litres of the solution at 480 ml/min. Cool tablets until exhaust temperature is 100° F. (38° C.). Apply 40 to 50 gm of carnauba wax.

Example One

Allyl mercaptan and diallyl disulfide are among the malodorous constituents of garlic breath. The purpose of this example is to quantitatively determine and compare the amounts of allyl mercaptan and diallyl disulfide present in garlic breath, over a 24 hour period, resulting from the consumption of garlic tablets according to the invention compared with an equivalent portion of fresh garlic.

Method

A comparative assay of garlic breath odor was performed on two subjects with two garlic tablets according to the invention and 2 cloves of fresh garlic (positive control). The subject's breath was collected at time 0 (prior to consumption of tablets or fresh garlic) and then at 0.5, 1, 2, 4, 8, and 24 hours. The tablets were swallowed whole and washed down with water. The fresh garlic was homogenized in 100 mL of water and swallowed, being washed down with another volume of water.

Breath of the test subjects was exhaled into 3.0 L Tedlar bags. A PDMS (polydimethylsiloxane) SPME (Solid Phase Microextraction) fibre was introduced to the inflated bag via a gas tight septa. Volatile components of the subjects breath were absorbed onto the surface of the SPME fibre for 30 minutes. The fibre was removed and thermally desorbed onto a GC Column (BPX5 1 µm film, 0.5 mm×50 m) with an inlet temperature of 260° C. in splitless mode. The GC oven was set at an initial temperature of 45° C. for 6 mins to allow focussing of the desorbed compounds.

To attain maximum sensitivity the mass spectrometer was set in SIM (selected ion monitoring) mode whereby only ions significant to the compounds allyl mercaptan and diallyl disulfide are scanned, thus enhancing the response for these compounds. For allyl mercaptan the ions 39, 45, 47, 59, 69, and 74 m/z, were selected in the elution time range. 4.6-15.0 mins. For diallyl disulfide the ions 81, 105, 113, 146 m/z were selected in the elution time range 15.0-23.5 mins. A major ion for both allyl mercaptan and diallyl disulfide is 41 m/z, however was not included in the SIM ions as its common occurrence in human breath negates any gain in selectivity. The peak areas of allyl mercaptan and diallyl disulfide are measured and calculated to mass units by reference to external calibration standard curves.

BRIEF DESCRIPTION OF THE SEVERAL VIEWS OF THE DRAWINGS

Results

Figure 1:
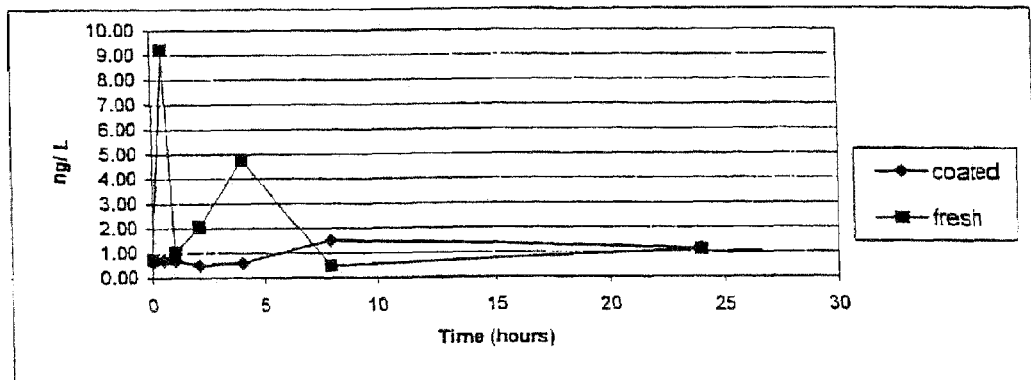
FIG. 1 is a chart showing the results obtained for diallyl sulfide in breath from coated garlic tables according to the invention and from fresh garlic.
Figure 2:
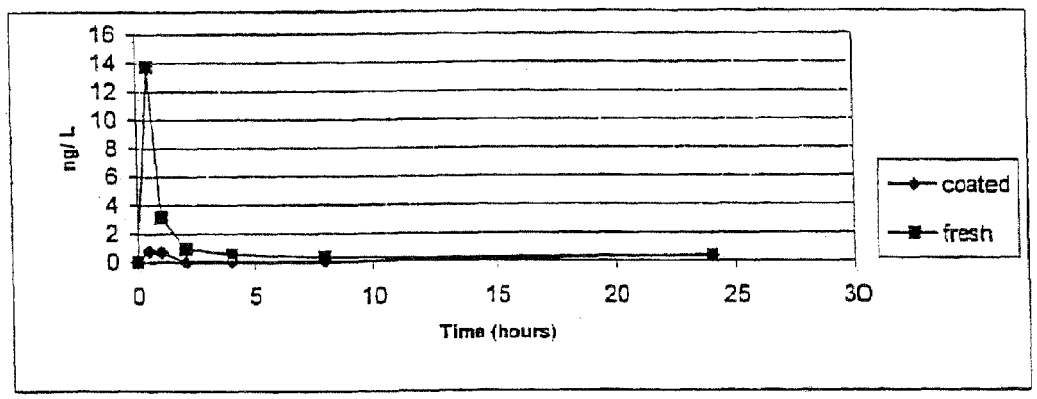
FIG. 2 is a chart showing the results obtained for allyl mercaptan in breath from coated garlic tables according to the invention and from fresh garlic.

Allyl mercaptan present in subject breath in the test period following consumption of enteric/mint coated garlic tablets is markedly lower than the levels detected in fresh garlic breath. Diallyl disulfide exhibits two, maximia at 30 minutes and at 4 hours for the fresh garlic indicating release from the stomach and subsequent release through the blood from the intestine. Diallyl disulfide is present in very low levels in breath from the enteric/mint coated tablets until 4-8 hours at which time it is released into the blood via the intestine. The level of diallyl disulfide is however significantly lower than levels detected in fresh garlic breath.

The signal to noise ratio has been determined from the calibration standards data. Diallyl disulfide peaks are confidently integrated to 3 ng/L and are detectable to 0.3 ng/L. Allyl mercaptan peaks are confidently integrated to 6 ng/L and detectable to ~0.6 ng/L. Peaks included in the results which have values lower than the integration limits are presented as indicative data only.

Conclusions

Humans can detect odors where there is above 2 ng/L of the compound present. Since the tablets according to the invention do not produce either of the tested compounds at a level above 2 ng/L, example one illustrates that garlic tablets according to the invention have substantially reduced the garlic odor.

Example Two

This example compares odor constituents of subject breath during consumption period of garlic tablets without mint extract in the enteric coating (control) and garlic tablets containing mint extract in the enteric coating according to the invention. In addition, this example compares the influence of peppermint extract alone on subject breath odor components after consumption of fresh garlic homogenate. The aim of this study was to confirm that the deodorizing effect of the invention was not simply due to either the enteric coating or mint extract alone.

Method

Comparison of Breath from Consumption of Control Enteric Coated Tablets and Garlic Tablets According to the Invention.

A comparative assay of garlic breath odor was performed on one subject consuming two garlic tablets (either control or garlic tablets according to the invention) for three days. The subject's breath was collected at time 0 (prior to consumption of tablets) and then at 4, 8, 24, 26, 28, 32, 48, 50, and 54 hours. The tablets were swallowed whole and washed down with water each morning after the first breath sample for the day was collected. The fresh garlic is homogenized in 100 mL of water and swallowed, being washed down with another volume of water.

Comparison of Breath from Consumption of Garlic Homogenate with and without Added Peppermint Extract For the control sample two cloves of fresh garlic were homogenised in 100 mL of water and swallowed, being washed down with another volume of water. For the test sample ~20-30 mgs (3 drops) of peppermint oil were added to a homogenate of 2 garlic cloves and 100 mL of water. This sample was imbibed as above. Subject breath was collected for analysis at time 0, 0.5, 1, 2, 4, 8, and 24 hours.

Analytical methodology

Breath of the test subjects was exhaled into 3.0 L Tedlar bags. A PDMS (Polydimethylsiloxane) SPME (Solid Phase Microextraction) fibre was introduced to the inflated bag via a gas tight septa. Volatile components of the subjects breath were absorbed onto the surface of the SPME-fibre for 30 minutes. The fibre was removed and thermally desorbed onto a GC Column (BPX5 1 μm film, 0.5 mm×50 m) with an, inlet temperature of 260° C. in splitless mode. The GC oven was set at an initial temperature of 45° C. for 6 mins to allow focussing of the desorbed compounds.

To attain maximum sensitivity the mass spectrometer was set in SIM (selected ion monitoring) mode, whereby only ions significant to the compounds allyl mercaptan and diallyl disulfide are scanned, thus enhancing the response for these compounds. For allyl mercaptan the ions 39, 45, 47, 59, 69, 74, and 88 m/z were selected in the elution time range 4.6-15.0 mins. For diallyl disulfide the ions 81, 105, 113, 146 m/z were selected in the elution time range 15.0-23.5 mins. The mass ion for both allyl mercaptan and diallyl disulfide is 41 m/z. It could not be included in the SIM ions as it is ubiquitous in human breath. The peak areas of allyl mercaptan and diallyl disulfide are measured and calculated to mass units by reference to external calibration standard curves.

Results

Comparison of Breath from Consumption of Control Enteric Coated Tablets and Garlic Tablets According to the Invention.

Figure 3:
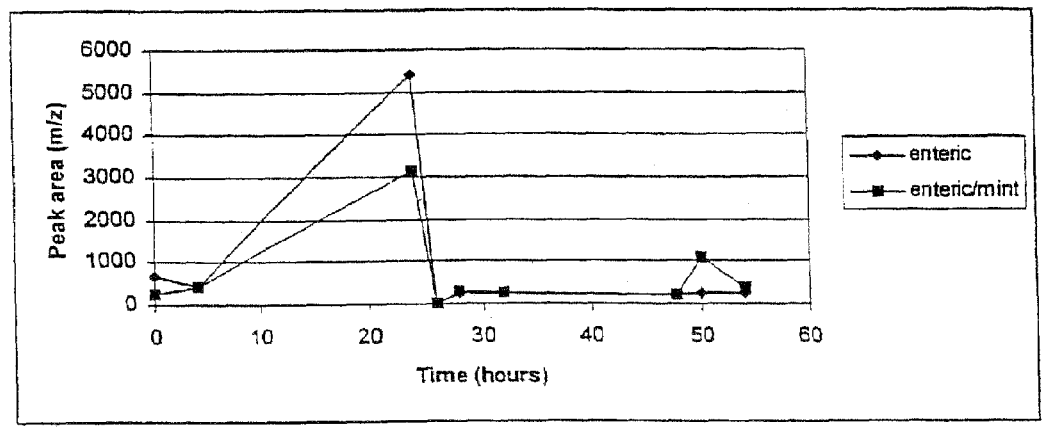
FIG. 3 is a chart showing the results obtained for diallyl disulfide in breath from control tablets (enteric) and garlic tablets according to the invention (enteric/mint).

FIG. 3 shows the results obtained for diallyl disulfide in breath from control tablets (enteric) and garlic tablets according to the invention (enteric/mint).

Figure 4:
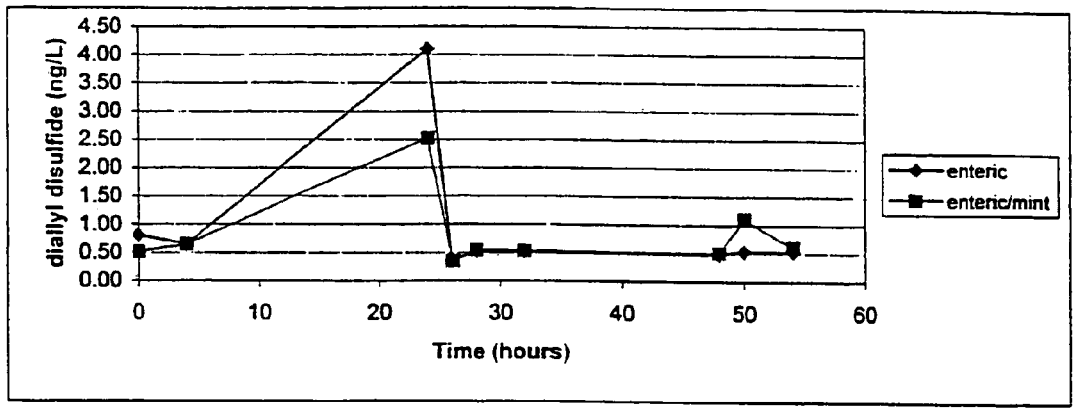
FIG. 4 is a chart showing the results obtained for diallyl disulfide in breath from control tablets (enteric) and garlic tablets according to the invention (enteric/mint) expressed in peak areas.

FIG. 4 shows the results obtained for diallyl disulfide in breath from control tablets (enteric) and garlic tablets according to the invention (enteric/mint) expressed in peak areas.

The SIM conditions used are specifically targeted at allyl mercaptan and diallyl disulfide. It is likely that the major ions present in the fragmentation patterns of these two compounds are present in the mass spectra of other related garlic odor compounds. In the comparative assay of enteric coated tablets levels of allyl mercaptan and diallyl disulfide were too low to explain the strong breath odor and sulfurous flavors which were intermittently present during this and other trials. However at least two other peaks occurring either side of allyl mercaptan exhibited trends correlating to the observed episodes of garlic breath. These occur at retention times of 7.64 and 8.01 minutes. Comparative trends of these two compounds are compared in charts 5 & 6.

Figure 5:
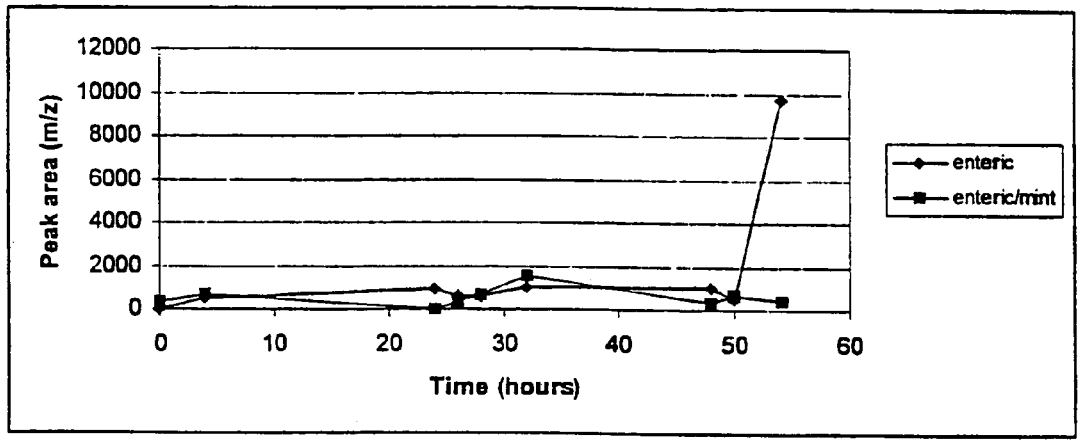
FIG. 5 is a chart showing the results obtained for compound RT-7.64 in breath from control tablets (enteric) and garlic tablets according to the invention (enteric/mint).

FIG. 5 shows the results obtained for compound RT-7.64 in breath from control tablets (enteric) and garlic tablets according to the invention (enteric/mint).

Figure 6:
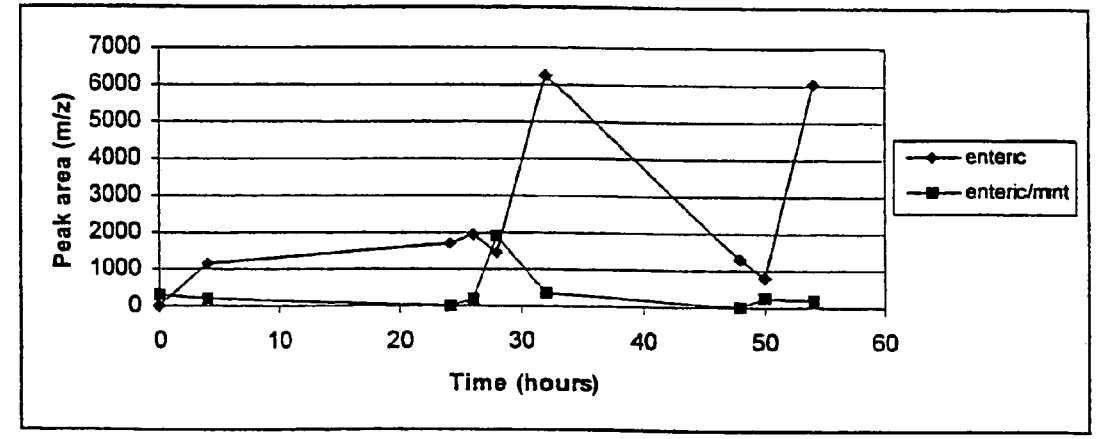
FIG. 6 is a chart showing the results obtained for compound RT 8.01 in breath from control tablets (enteric) and garlic tablets according to the invention (enteric/mint).

FIG. 6 shows the results obtained for compound RT 8.01 in breath from control tablets (enteric) and garlic tablets according to the invention (enteric/mint).

FIGS. 5 & 6 clearly identify the that peaks RT 7.64 & RT 8.01 varied according to the tablet consumed. After 50 hours peak RT 7.64 increases substantially but only in the control tablet. Analysis of breath after garlic tablets according to the invention did not show a similar increase in peak 7.64. Similarly after 30 hours peak RT 8.01 was only present after consumption of the control garlic tablet without aqueous mint extract in the enteric coat.

FIGS. 3 to 6 clearly demonstrate that the garlic tablets according to the invention continue to inhibit the release of objectionable sulfur compounds for a longer period than the Control enteric coated tablets. Since tablets according to the invention do not produce either of the tested compounds at a level above 2 ng/L, example two illustrates that tablets according to the invention substantially reduced garlic odor. These results also illustrate that inclusion of aqueous extract in the external enteric coat dramatically reduces garlic breath odour compared to an identical tablet with only the enteric coating.

Comparison of Breath from Consumption of Garlic Homogenate with and without Added Peppermint Extract To determine if the odor reducing effect of the current invention was simply due to addition of peppermint, a garlic homogenate equivalent to the amount of garlic contained in the tablet was consumed.

Figure 7:
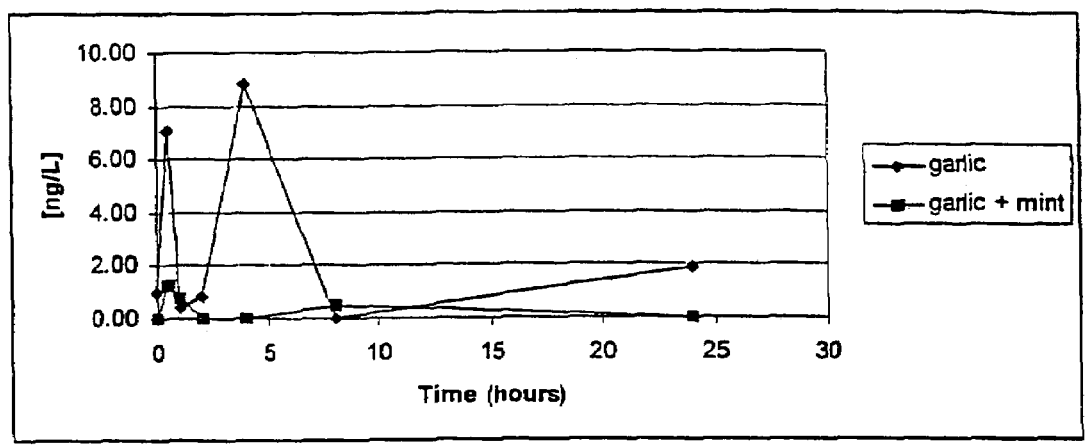
FIG. 7 is a chart showing the results obtained for diallyl disulfide in breath from fresh garlic and fresh garlic with peppermint extract.

FIG. 7 shows the results obtained for diallyl disulfide in breath from fresh garlic and fresh garlic with peppermint extract.

Figure 8:
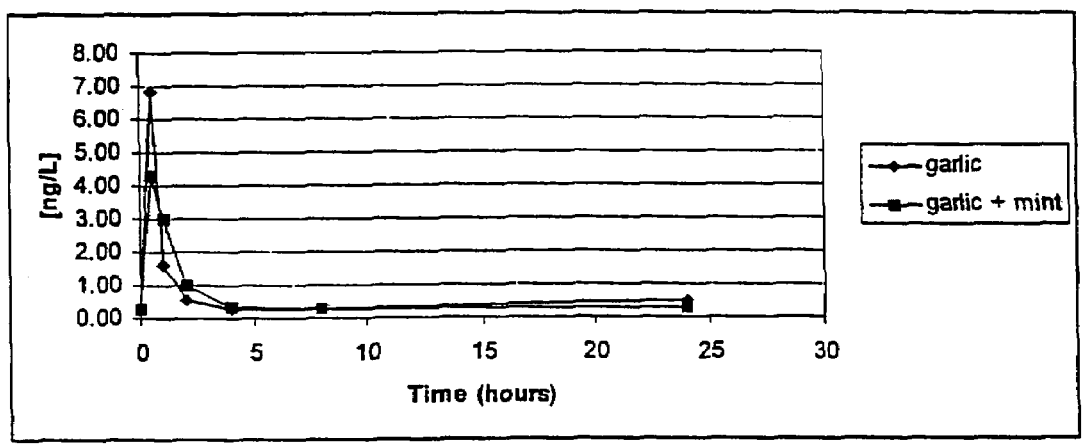
FIG. 8 is a chart showing the results obtained for allyl mercaptan in breath from fresh garlic and fresh garlic with peppermint extract.

FIG. 8 shows the results obtained for allyl mercaptan in breath from fresh garlic and fresh garlic with peppermint extract.

FIGS. 7 and 8 clearly show that whilst the peppermint extract when included at many times the level incorporated into the enteric coating does reduce the release of diallyl sulfide, it does not have any odor reductive effects in relation to allyl mercaptan.

Conclusion

Example 2 clearly demonstrates that the standard enteric coating alone and the peppermint extract alone do not effectively reduce garlic odor over extended periods of time. However, when an enteric coating is applied to the garlic tablet which contains peppermint extract, if a user consumes the garlic tablets daily then garlic odor is effectively reduced for a more than two days.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The invention claimed is:

1. A garlic supplement comprising:
   (a) one or more cores comprising garlic and one or more deodorizers selected from the group consisting of extracts derived from *Lamiaceae* plants, natural flavours derived from *Lamiaceae* plants and oils derived from *Lamiaceae* plants; and
   (b) an enteric coating encasing the core(s) which is insoluble at pH less than about 5 but soluble at a pH greater than about 5, wherein the enteric coating comprises one or more deodorizers selected from the group consisting of extracts derived from *Lamiaceae* plants, natural flavors derived from *Lamiaceae* plants, and oils derived from *Lamiaceae* plants.

2. A garlic supplement according to claim 1 wherein the garlic supplement is in a form selected from the group consisting of a tablet cross-linked capsule, gelatin capsule, suspensions, emulsions, enteral feeds, functional foods or microparticles.

3. A garlic supplement according to claim 1 wherein the core(s) is in a form selected from the group consisting of liquids, solids, fluids, gels and mixtures thereof.

4. A garlic supplement according to claim 1 wherein the garlic is in a form selected from the group consisting of fresh garlic, dry powder, oils, macerates, extracts, aged extracts, steam distilled oils and mixtures thereof.

5. A garlic supplement according to claim 4 wherein the garlic is in the form of a dry powder.

6. A garlic supplement according to claim 1 wherein the enteric coating is selected from the group consisting cellulose, methylcellulose, natural polymers, synthetic polymers, cross-linked gelatin and mixtures thereof.

7. A garlic supplement according to claim 6 wherein the enteric coating is selected from cellulose or methylcellulose or mixtures thereof.

8. A garlic supplement according to claim 1 wherein the thickness of the enteric-coating is not greater than about 0.5 mm.

9. A garlic supplement according to claim 1 wherein the deodorizer present in the enteric coating is from about 0.5 to about 1.0 weight % of the total weight of the enteric coating.

10. A garlic supplement according to claim 9 wherein the deodorizer present in the enteric coating is about 0.6 weight % of the total weight of the enteric coating.

11. A garlic supplement according to claim 1 which further comprises an external coating applied over the enteric coating.

12. A garlic supplement according to claim 11 wherein the external coating has a thickness in the range of from 0.001 mm to 1.500 mm.

13. A garlic supplement according to claim 11 wherein the external coating comprises one or more coating agents selected from the group consisting of microcrystalline waxes, carnauba wax, polyvinylpyrroldidone, sugars and mixtures thereof.

14. A garlic supplement according to claim 11 wherein the external coating further comprises a deodorizer.

15. A garlic supplement according to claim 1 wherein the deodoriser is present in an amount in the range of 0.5 to 1.0% by total weight of the garlic supplement.

16. A garlic supplement according to claim 15 wherein the amount of deodorizer is about 0.6% by total weight of the garlic supplement.

17. A garlic supplement according to claim 1 wherein upon consumption of the garlic supplement by a human subject, the presence of at least one diallyl sulphide and allyl mercaptan in the breath of the subject does not exceed a level of 2 ng/l over a twenty four hour period.

18. A garlic supplement comprising:
   (a) one or more cores comprising garlic and one or more deodorizers selected from the group consisting of extracts derived from *Lamiaceae* plants, extracts derived from parsley seed, extracts derived from green tea, aqueous extracts derived from *Lamiaceae* plants, aqueous extracts derived from parsley seed, aqueous extracts derived from green tea, natural flavors derived from *Lamiaceae* plants, natural flavors derived from parsley seed, natural flavors derived from green tea, oils derived from *Lamiaceae* plants, oils derived from parsley seed, oils derived from green tea, and mixtures thereof; and
   (b) an enteric coating encasing the core(s) which is insoluble at pH less than about 5 but soluble at a pH greater than about 5, wherein the enteric coating comprises one or more deodorizers selected from the group consisting of extracts derived from *Lamiaceae* plants, extracts derived from parsley seed, extracts derived from green tea, aqueous extracts derived from *Lamiaceae* plants, aqueous extracts derived from parsley seed, aqueous extracts derived from green tea, natural flavors derived from *Lamiaceae* plants, natural flavors derived from parsley seed, natural flavors derived from green tea, oils derived from *Lamiaceae* plants, oils derived from parsley seed, oils derived from green tea, and mixtures thereof.

* * * * *